United States Patent
Erkamp et al.

(10) Patent No.: US 11,864,948 B2
(45) Date of Patent: *Jan. 9, 2024

(54) NEEDLE WITH THIN FILM SENSORS

(71) Applicant: KONINKLIJKE PHILIPS N.V., Eindhoven (NL)

(72) Inventors: Ramon Quido Erkamp, Swampscott, MA (US); Ameet Kumar Jain, Boston, MA (US); Francois Guy Gerard Marie Vignon, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 233 days.

This patent is subject to a terminal disclaimer.

(21) Appl. No.: 17/207,708

(22) Filed: Mar. 21, 2021

(65) Prior Publication Data

US 2021/0204911 A1 Jul. 8, 2021

Related U.S. Application Data

(63) Continuation of application No. 15/301,726, filed as application No. PCT/IB2015/052362 on Mar. 31, 2015, now Pat. No. 10,952,704.

(Continued)

(51) Int. Cl.
*A61B 8/00* (2006.01)
*A61B 17/34* (2006.01)
(Continued)

(52) U.S. Cl.
CPC .......... *A61B 8/4494* (2013.01); *A61B 5/6848* (2013.01); *A61B 8/0841* (2013.01);
(Continued)

(58) Field of Classification Search
CPC .. A61B 2017/3413; A61B 2017/00526; A61B 2090/3925; A61B 17/3417;
(Continued)

(56) References Cited

U.S. PATENT DOCUMENTS

| | | |
|---|---|---|
| 2,588,292 A | 3/1952 | Rittner |
| 4,829,814 A | 5/1989 | Suzuki |

(Continued)

FOREIGN PATENT DOCUMENTS

| | | |
|---|---|---|
| JP | S58207798 A | 12/1983 |
| JP | 2005002434 A | 1/2005 |

(Continued)

OTHER PUBLICATIONS

Barr, Richard G. "Improved Needle Visualization with Electronic Beam Steering", Ultrasound Quarterly, vol. 28, No. 2, Jun. 2012.

(Continued)

*Primary Examiner* — Ashley K Buran
*Assistant Examiner* — Helene Bor

(57) ABSTRACT

A sensor device includes a flexible planar strip with a plurality of layers is described. The flexible planar strip is configured to at least partially encapsulate a medical device. The flexible planar strip includes a first dielectric layer, a second dielectric layer, and a patterned conductive layer including a sensor electrode disposed on the second dielectric layer. According to one aspect an ultrasound sensor including a piezoelectric polymer. The ultrasound sensor is disposed on the sensor electrode such that a first surface of the ultrasound sensor is in electrical contact with the sensor electrode and such that a second surface of the ultrasound sensor is exposed for making electrical contact with a medical device.

20 Claims, 7 Drawing Sheets

Related U.S. Application Data

(60) Provisional application No. 61/978,223, filed on Apr. 11, 2014.

(51) Int. Cl.
| | | |
|---|---|---|
| *A61B 90/00* | (2016.01) | |
| *A61B 5/00* | (2006.01) | |
| *A61B 8/08* | (2006.01) | |
| *B06B 1/06* | (2006.01) | |
| *A61B 17/00* | (2006.01) | |

(52) U.S. Cl.
CPC .......... *A61B 17/3417* (2013.01); *A61B 90/39* (2016.02); *B06B 1/0688* (2013.01); *A61B 8/4444* (2013.01); *A61B 17/3403* (2013.01); *A61B 2017/00526* (2013.01); *A61B 2017/3413* (2013.01); *A61B 2090/3925* (2016.02); *A61B 2090/3929* (2016.02); *A61B 2562/164* (2013.01)

(58) Field of Classification Search
CPC ..... A61B 90/39; A61B 8/4494; A61B 5/6848; A61B 8/4444; A61B 8/4483; A61B 8/12; A61B 2562/164
See application file for complete search history.

(56) References Cited

U.S. PATENT DOCUMENTS

| | | | | |
|---|---|---|---|---|
| 4,911,172 | A * | 3/1990 | Bui | B06B 1/0688 600/461 |
| 5,515,848 | A * | 5/1996 | Corbett, III | H01R 13/50 607/116 |
| 5,515,853 | A | 5/1996 | Smith | |
| 5,647,870 | A | 7/1997 | Kordis | |
| 5,797,849 | A | 8/1998 | Vesely | |
| 5,830,144 | A | 11/1998 | Vesely | |
| 6,217,518 | B1 * | 4/2001 | Holdaway | A61B 5/6848 600/443 |
| 6,253,770 | B1 | 7/2001 | Acker | |
| 6,490,474 | B1 | 12/2002 | Willis | |
| 7,034,326 | B2 | 4/2006 | Noguchi | |
| 8,148,686 | B2 | 4/2012 | Ryhanen | |
| 8,386,009 | B2 | 2/2013 | Lindberg | |
| 8,605,084 | B2 | 12/2013 | Castelli | |
| 8,696,917 | B2 | 4/2014 | Petisce | |
| 8,700,118 | B2 | 4/2014 | Oster | |
| 8,825,128 | B2 | 9/2014 | Ylostalo | |
| 9,226,800 | B2 | 1/2016 | Burg | |
| 2002/0002371 | A1 | 1/2002 | Acker | |
| 2002/0032380 | A1 | 3/2002 | Acker | |
| 2006/0114009 | A1 * | 6/2006 | Root | G01R 1/18 324/750.27 |
| 2006/0235314 | A1 * | 10/2006 | Migliuolo | A61B 1/0011 600/549 |
| 2007/0285868 | A1 * | 12/2007 | Lindberg | A61B 5/0245 600/382 |
| 2009/0297574 | A1 * | 12/2009 | Ahn | A61B 5/412 604/27 |
| 2010/0204643 | A1 | 8/2010 | Sarvazyan | |
| 2010/0262140 | A1 | 10/2010 | Watson | |
| 2011/0270081 | A1 * | 11/2011 | Burg | A61B 34/20 600/424 |
| 2013/0066194 | A1 * | 3/2013 | Seter | A61B 5/062 29/846 |
| 2015/0148703 | A1 * | 5/2015 | Fiebig | A61B 10/0275 600/567 |
| 2017/0172544 | A1 | 6/2017 | Erkamp | |

FOREIGN PATENT DOCUMENTS

| | | |
|---|---|---|
| JP | 2010531718 A | 9/2010 |
| WO | 199822179 A2 | 5/1998 |
| WO | 2009006335 A1 | 1/2009 |

OTHER PUBLICATIONS

Nichols, Kremer et al "Changes in Ultrasonographic Echogenicity and Visibility of Needles with Changes in Angles of Insonation", J Vasc Interv Radiology, vol. 14, No. 12, 2003.

Cheung, Stphanic et al "Enhancement of needle visibility in ultrasound-guided percutaneous procedures", Ultrasound in Medicine & Biology, vol. 30, Issue 5, May 2004—Abstract Only.

* cited by examiner

NEEDLE WITH THIN FILM SENSORS

CROSS-REFERENCE TO RELATED APPLICATIONS

This application is a continuation of U.S. application Ser. No. 15/301,726 filed on Oct. 4, 2016, which is a U.S. National Phase application under 35 U.S.C. § 371 of International Application No. PCT/IB2015/052362, filed on Mar. 31, 2015, which claims the benefit of U.S. Provisional Patent Application No. 61/978,223, filed on Apr. 11, 2014. These applications are each hereby incorporated by reference herein in their entirety.

BACKGROUND

Technical Field

This disclosure relates to medical instruments and more particularly to a system and method for applying ultrasound receivers on a device using planar thin film methods.

Description of the Related Art

In ultrasound imaging, the visibility of the needle is often very poor due to the specular nature of the needle surface that reflects beams away from the imaging probe. To alleviate this problem some needle manufacturers have produced needles with special echogenic coatings, but the visualization improvement is limited. Ultrasound imaging system manufacturers have developed algorithms that use multiple imaging beams from varied angles, but improvement is limited and such a strategy is primarily suited only for linear arrays. Both strategies do not help when the needle is inserted perpendicular to the imaging plane, or the needle path has a small offset relative to the imaging plane.

One solution that has been proposed to visualize the tip of interventional tools such as needles, but also catheters, is to add ultrasound receivers near the tip of the tool. While the imaging beam sweeps the field of view, the signals from the sensors indicate how close the beams are getting to the sensor. This information is used to calculate sensor position relative to the ultrasound image with positional accuracy exceeding 0.5 mm, even under conditions where the needle is not visible in the ultrasound image. The sensor needs to not interfere with the functionality of the device (e.g., an automatic biopsy device), that is, not block the lumen, not interfere with the mechanics, etc.

SUMMARY

In accordance with the present principles, a sensor device includes a flexible planar strip including a plurality of layers. The strip is configured to at least partially encapsulate a medical device. The strip includes a first dielectric layer, a second dielectric layer formed on the conductive shield layer; and a patterned conductive layer including a sensor electrode.

According to some implementations, the sensor device includes a flexible planar strip including a plurality of layers, the strip being configured to spirally wrap around a medical device to at least partially encapsulate the medical device. The strip includes a first dielectric layer of the strip having at least one angled end portion and including at least one cross-strip extending transversely from a longitudinal dimension of the strip. A bottom electrode and a bottom electrode trace, which connects to the bottom electrode, are formed on the first dielectric layer. A piezoelectric layer is formed on the bottom electrode. A top electrode and a top electrode trace, which connects to the top electrode, are formed on the piezoelectric layer.

A method for applying a sensor to a medical device includes providing a flexible planar strip having a plurality of layers including dielectric materials and sensor components; wrapping the flexible planar strip about a medical device to at least partially encapsulate the medical device; and securing the strip to the medical device using a securing feature over the strip such that at least one sensor device is provided on the medical device by application of the strip on the medical device.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
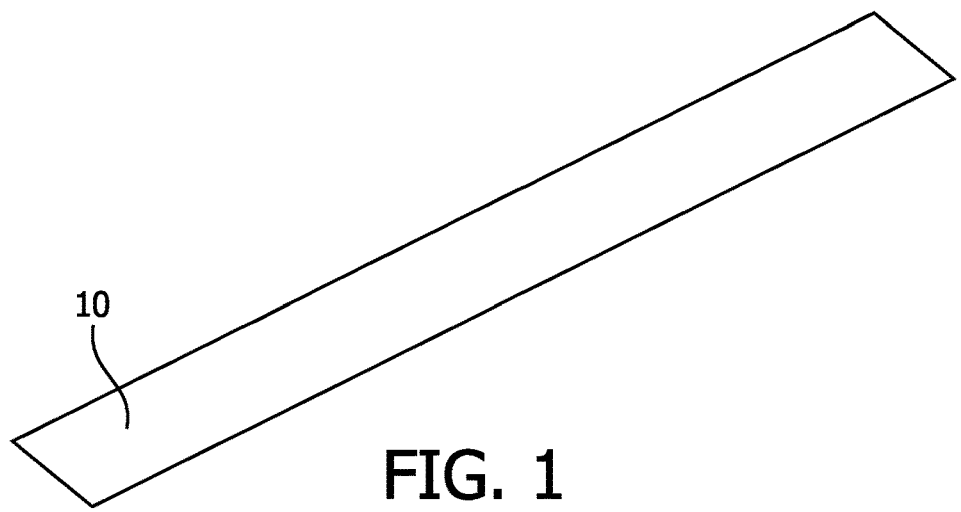
FIG. 1 is a perspective view showing a flexible planar dielectric layer for forming a low profile conformal sensor device in accordance with the present principles.

In accordance with the present principles, systems, devices and methods are provided for applying a sensor or sensors to a needle (or other device) to implement ultrasound guidance or tracking of the needle or device. The present principles provide a needle, device or system that includes one or more low profile sensors at very low per device cost and permits scaling for mass production to maintain low cost. In one embodiment, an interconnect for the sensor may be mass manufactured on a large planar thin film sheet (with a repeating pattern) and subsequently cut into thin strips. Methods are described for attaching these strips to the device. In one method, a highly bendable/flexible material is employed for the sheet, and the sheet is wrapped about a circumference of the device. In another method, a strip is wrapped around the needle in a spiraling manner. In these and other methods, a sensor device is formed on a thin planar film, which is to be mounted on the device.

The ultrasound sensors may be formed on a thin film planar sheet by building dielectric layers and patterning conductors such that the entire sensor (or a portion of the sensor) is formed prior to its mounting on the device. The needle or other device may be fabricated using a piezoelectric polymer, e.g., polyvinylidene fluoride (PVDF) or polyvinylidene fluoride trifluoroethylene (P(VDF-TrFE)). P(VDF-TrFE). These materials can be dissolved in acetone and applied to the planar sheet or to the medical device through an evaporative process. The sensors are high impedance and can be modeled as a voltage source in series with a small capacitor (e.g., 2.2 pF). Such a sensor is very sensitive to capacitive loading of the electrical interconnect, and special capacitance cancelling electronics (similar to, e.g., a driven shield technique) can be employed to avoid large signal loss. A wire or trace carrying the signal preferably is shielded (e.g., includes an electric shield around the conductor). This may be accomplished using a stripline configuration.

It should be understood that the present invention will be described in terms of medical instruments; however, the teachings of the present invention are much broader and are applicable to any instrument that can accept a low profile sensor. In some embodiments, the present principles are employed in tracking or analyzing complex biological or mechanical systems. In particular, the present principles are applicable to internal tracking procedures of biological systems and are applicable for procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a perspective view of a dielectric layer 10 is shown in accordance with one embodiment. The dielectric layer 10 may be formed as a sheet and represents and outer biocompatible insulation layer. The biocompatible insulation material for layer 10 may include Mylar, pressure sensitive adhesive films, polyester films, polyimide films, parylene, polyurethane, etc. The sheet on which the dielectric layer 10 is formed may be first manufactured on a large planar thin film sheet. One sheet may include a plurality of structures. Then, individual units can be cut from the sheet using, for example, laser cutting, stamping, etc. The dielectric layer 10 may be the first layer in the sheet as the layers and components will be constructed from an outermost layer to an innermost layer; however, the fabrication order may be reversed or otherwise changed, as needed. FIG. 1 shows a single unit as cut from such a larger sheet to illustratively show the fabrication of the single unit. The first biocompatible dielectric layer 10 will form the outer layer of a sensor equipped needle or other device. The dielectric layer 10 may be about 25-50 microns thick although other thicknesses may be employed.

Figure 2:
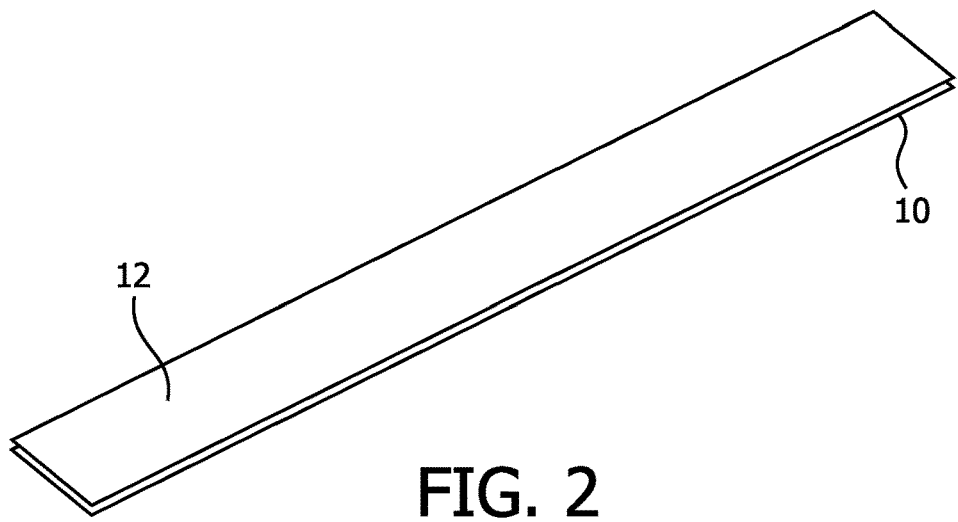
FIG. 2 is a perspective view showing the device of FIG. 1 having a conductive shield layer formed thereon in accordance with the present principles.

Referring to FIG. 2, a conductive layer 12 is formed on layer 10. The conductive layer 12 will form an outer shield for the sensor equipped needle or other device. The conductive layer 12 may include a foil adhered to layer 10, include conductive ink, include an evaporated metal, etc.

Figure 3:
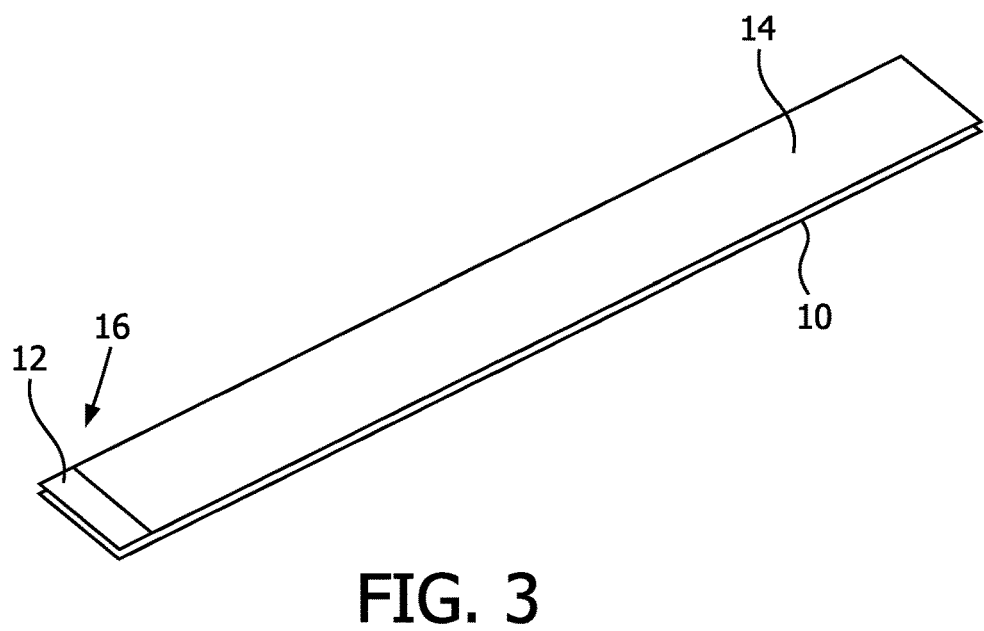
FIG. 3 is a perspective view showing the device of FIG. 2 having a middle insulating layer formed thereon in accordance with the present principles.

Referring to FIG. 3, a middle insulating layer 14 is deposited or formed over the conductive layer 12. At a hub end portion 16 of the strip, the middle insulating layer 14 does not extend to the end, so a small strip of the outer shield or conductive layer 12 remains exposed. This exposed end will eventually form a hub end ring electrode for the outer shield 12 that a needle connector (not shown) will connect to. The insulating layer 14 may be about 25-50 microns thick although other thicknesses may be employed.

Figure 4:
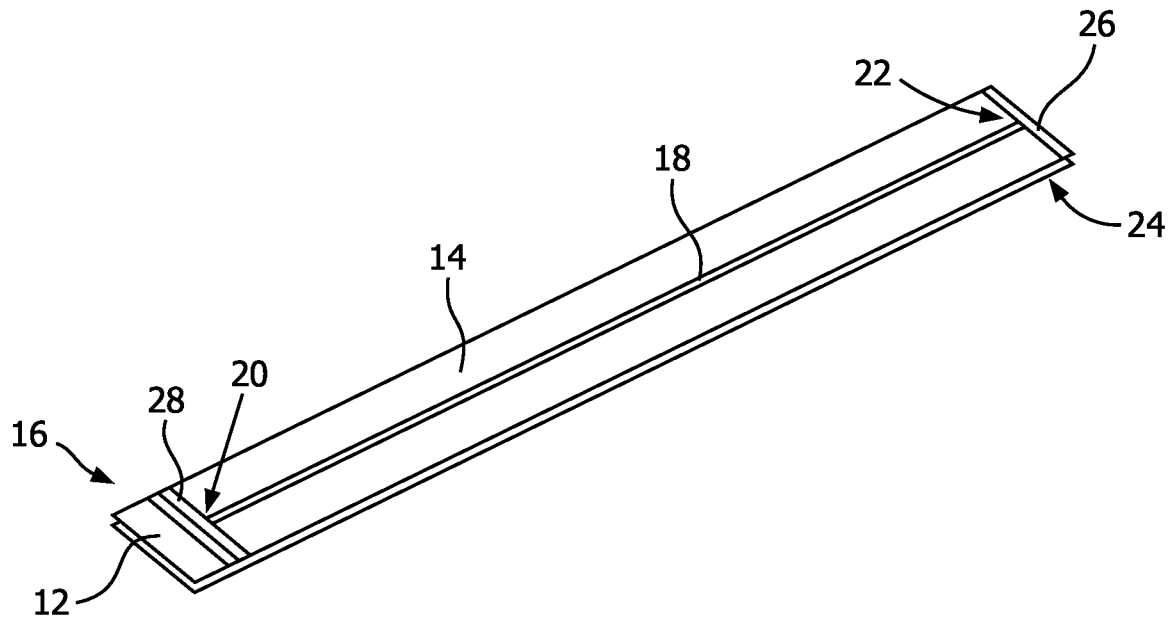
FIG. 4 is a perspective view showing the device of FIG. 3 having a top electrode, hub contact and trace formed on the middle insulating layer in accordance with the present principles.

Referring to FIG. 4, a conductive signal trace 18 is formed on the middle insulating layer 14. The trace 18 may be deposited and selectively etched to provide T-shaped end patterns 20, 22. At a tip end portion 24 (distal end portion), the T shaped end pattern 22 will form an electrode 26 that will cover the sensor to be formed. At the hub end portion 16 (proximal end portion), the T shaped section 20 will form a ring or hub electrode 28 that a needle connector uses to connect to the signal trace 18. The conductive signal trace layer may include a thickness from about less than on micron to a few microns, although other thicknesses may be employed. In one embodiment, the electrodes 26, 28 and the trace 18 may be printed using a conductive ink. Other processes may be employed as well such as, e.g., masked vapor deposition or vapor deposition and etching.

Figure 5:
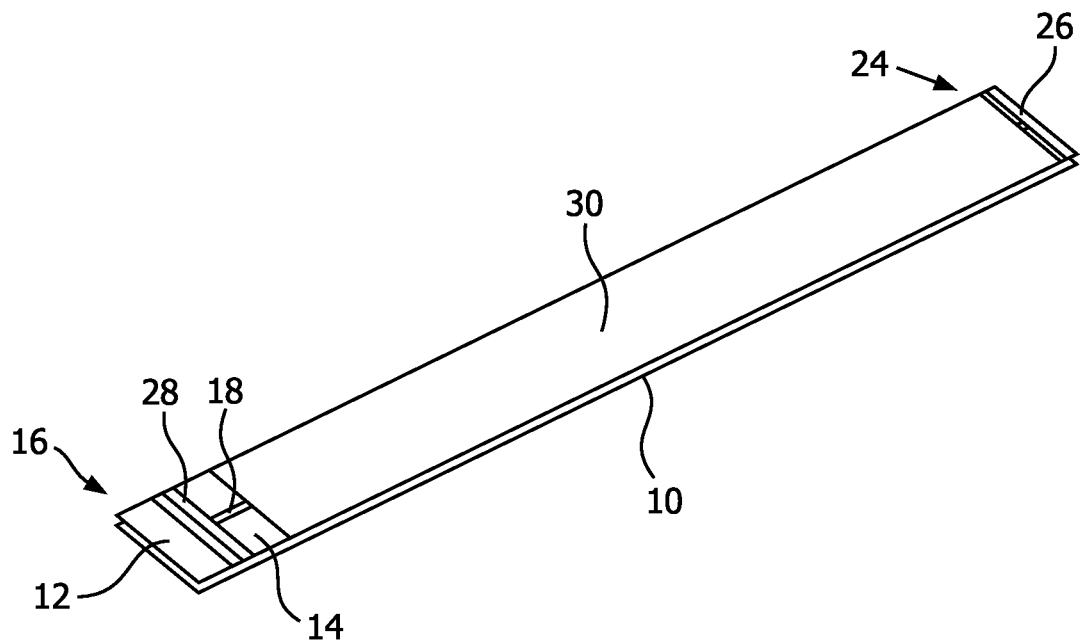
FIG. 5 is a perspective view showing the device of FIG. 4 having another dielectric layer (insulator) formed on the trace in accordance with the present principles.

Referring to FIG. 5, the signal trace 18 is then covered with another insulating layer 30. This insulating layer 30 will be on the side of the film that will come in contact with the needle or other device on which the sensor will be placed. At the tip end portion 24, the insulating layer 30 will leave the sensor electrode exposed, and at the hub end portion 16, the insulating layer 30 leaves the hub electrode 28 exposed. The insulating 18 may be about 25-50 microns thick although other thicknesses may be employed.

A structure 40 shown in FIG. 5 may include very thin but strong laminates for its layers, so that the structure 40 will not stretch and damage the conductive components formed therein. One or more of the insulating layers 10 may include, e.g., polyurethane, although other plastics or insulating materials may be employed. The conductive layer 12 may include a foil and may be aluminum, silver, gold or other biocompatible conductors. The structure 40 includes a width that may be less than a circumference of the needle or device on which it will be placed. In particularly useful embodiments, the width could be between, for example, about 20% of the circumference to about 90% the circumference.

Figure 6:
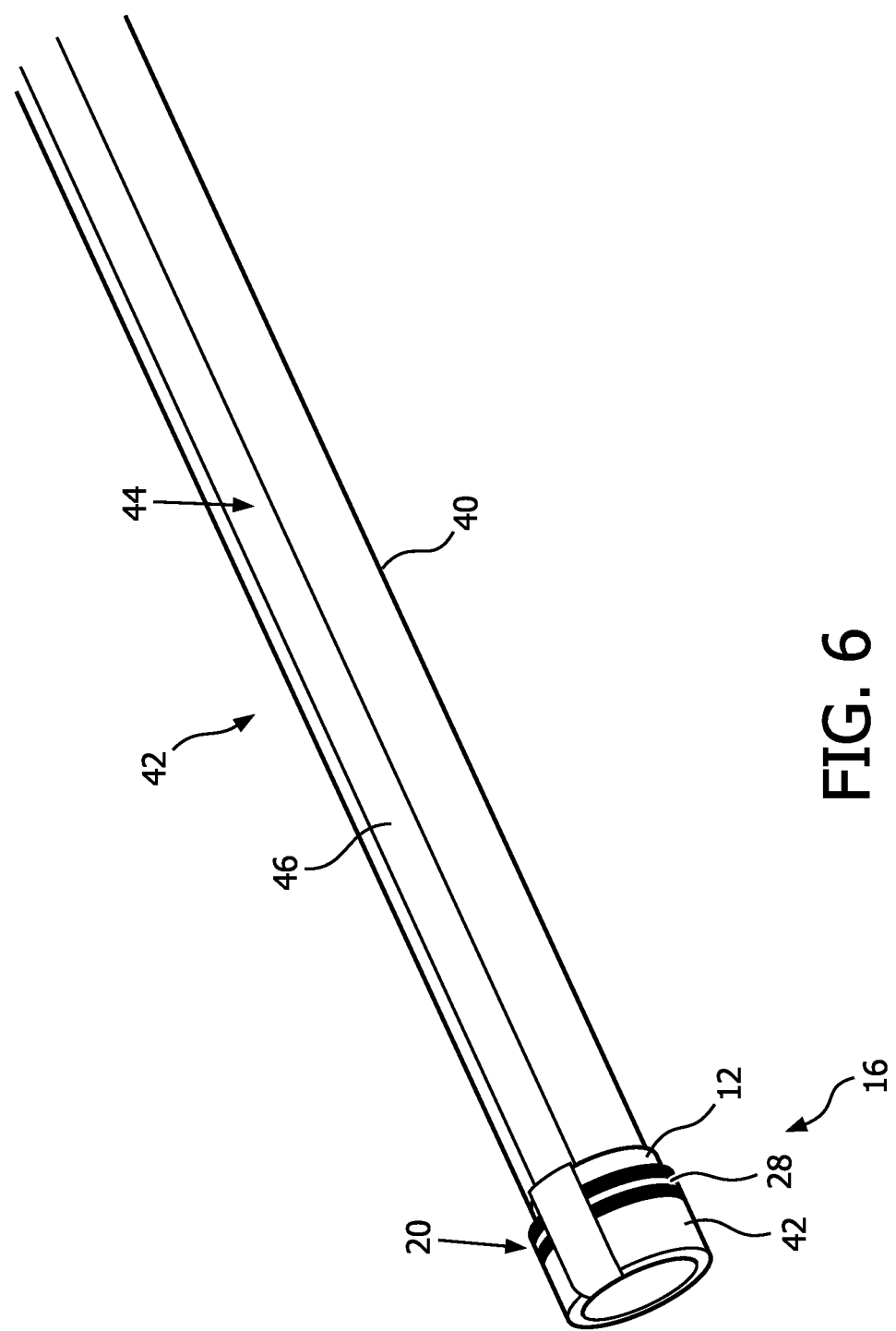
FIG. 6 is a perspective view showing the device of FIG. 5 being wrapped about a hub end of a needle in accordance with the present principles.

Referring to FIG. 6, the structure 40 can be attachable to a needle 42 by bending the structure 40 into a tubular shape. Layer 30 will be in contact with the needle 42 (or other device). The structure 40 includes a width that wraps around the needle 42 and is slightly smaller than a diameter of the needle 42. When installed on the needle 42, edges of the structure 40 form a gap 44 running along the length (or a substantial portion of the length) of the needle 42. The hub end portion 16 is shown in FIG. 6.

Between the edges of the gap 44, a different material may be applied that is highly elastic to form a stretchable tube that can slide over the needle 42. Application of an elastic strip 46 may, for example, be accomplished by gluing the elastic strip to the edges of the structure 40, or applying a glue that dries into an elastic material in the gap 44 when the structure 40 is wrapped around a template needle and then transferred to needle 42.

In one embodiment, the dielectric layer 10 in FIG. 1 may be formed from a material where the width covers a tube circumference (needle circumference), and makes the other insulator layers closer to the needle 42 (in the stack of layers) narrower (less width) so they make a more rigid structure 40.

At the hub end portion 16, a small portion of the conductive layer 12 and T-shape 20 may be folded back (cuffed) onto itself (e.g., folding the exposed strip onto itself at the very end before making it into a tube shape). This brings the contact points for the outer shield 12 and the T shape 20 signal trace from an inside surface of the formed tube to an outside of the tube, so that a clamp style connector can attach to these contact points.

Figure 7:
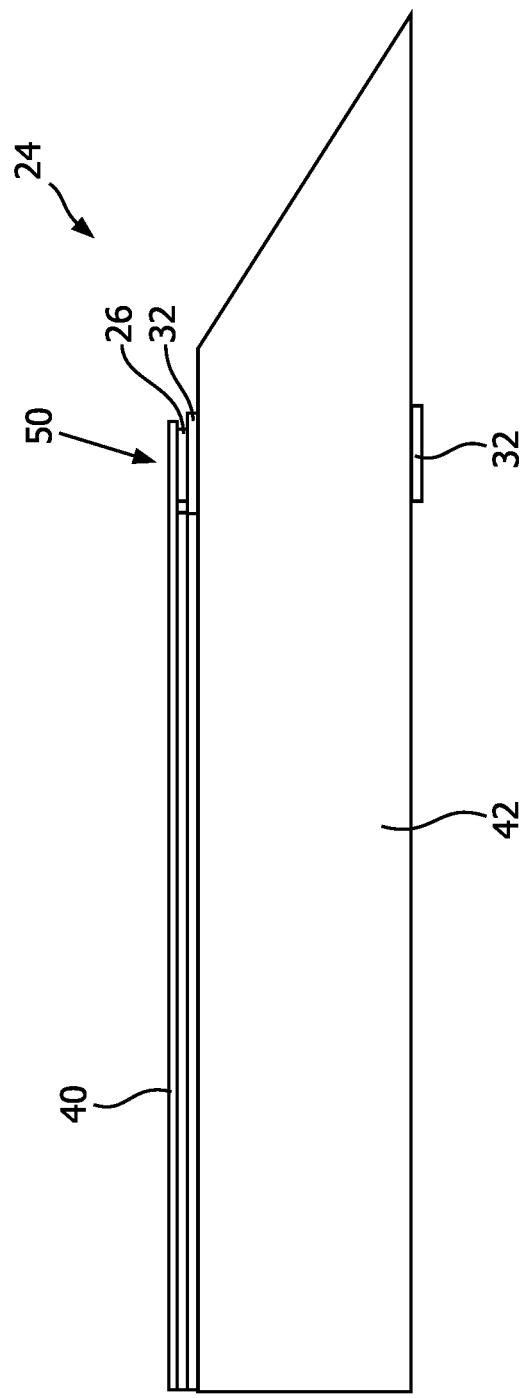
FIG. 7 is a side view showing the device of FIG. 5 being applied about a tip end of a needle with a piezoelectric material employed to form a sensor in accordance with the present principles.

Referring to FIG. 7, a single ring sensor 50 may be formed at the tip end portion 24 of the needle 42 in accordance with one embodiment. The needle 42 preferably includes a metal, such as a stainless steel although other surgically compatible materials may be employed. The tip end portion 24 (distal end portion) of the needle 42 may be coated with a piezoelectric copolymer 32. This may be achieved by employing a dip coating process. The metal needle 42 now serves as a bottom electrode for the copolymer sensor 50. The top electrode of the sensor 50 will be the electrode 26. In one embodiment, the copolymer may include a PVDF or P(VDF-TrFE) ring, although other suitable materials may be employed.

For the dielectric/insulating layers, e.g., layers 10, 14, 30 (FIG. 5), it is advantageous to select a material with a relatively low dielectric constant. For example, polytetrafluoroethylene (PTFE) with a dielectric constant of about 2.1 may be selected. However, the adhesion of PTFE to other materials may be an issue. Other materials, such as biocompatible polypropylene (dielectric constant 2.2) may be employed. Many plastics/polymers have a dielectric constant close to 3.0 and may also be employed. Polyurethane has a slightly higher 3.5 value and is attractive for use in the present applications because there are medical grade versions (used to coat implantable pacemakers). Further, polyurethane provides good adhesion to many materials with high smoothness and durability, and can be deposited in thin layers using appropriate solvents. Other materials may also be used.

The present principles can be extended to multiple sensors on a same needle. This permits a determination of an orientation of the needle and also a determination of the location of the needle tip without the need to place the sensor very close to the tip. Calculating the tip location based on signals from multiple sensors should also increase the measurement accuracy as well as provide an indication of confidence in the measurement. The cost is a slightly more complicated manufacturing process and a slight loss of signal because of the extra capacitive load of multiple sensors.

Referring to FIGS. 8-11, another embodiment includes a slanted strip 102 that can be attached to a needle or device using a spiral outer wrap. The slanted strip 102 in this embodiment includes embedded piezoelectric sensors and interconnects (traces).

Figure 8:
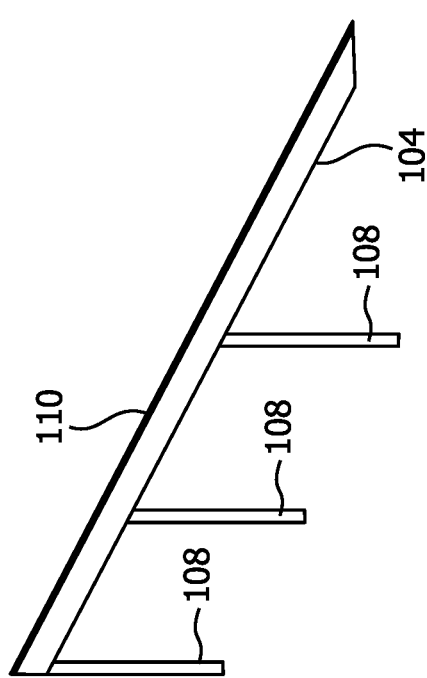
FIG. 8 is a top view of a slanted strip with cross-strips for forming a spirally wrapped sensor device in accordance with the present principles.

Referring to FIG. 8, an insulator 104 in the form of the slanted strip 102 includes thongs or cross-strips 106. The cross-strips 106 will include the sensors and are angled relative to the strip 102 so that when the strip 102 is lightly spirally wound about a needle (not shown), the cross-strips 106 will form rings around the needle. The insulator 104 may include one or more of the dielectric materials described above, e.g., polyurethane, Mylar, etc. The strip 102 includes an acutely slanted end portion 103 to enable a starting position for spirally wrapping the strip on the medical device.

Figure 9:
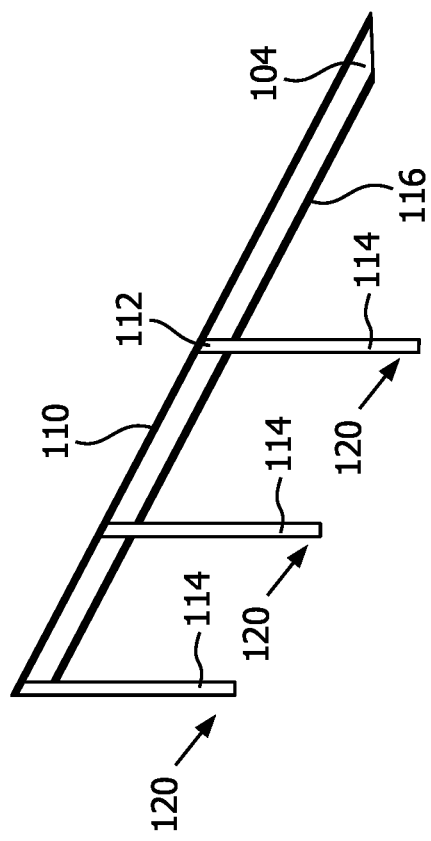
FIG. 9 is a top view showing the device of FIG. 8 with bottom electrodes (and traces) being applied in accordance with the present principles.

Referring to FIG. 9, a bottom electrode or electrodes 108 are formed along with a trace or traces 110 connecting the bottom electrodes 108. The conductive material for the bottom electrodes 108 and traces 110 may include conductive ink, evaporated metals, conductive polymers, etc.

Figure 10:
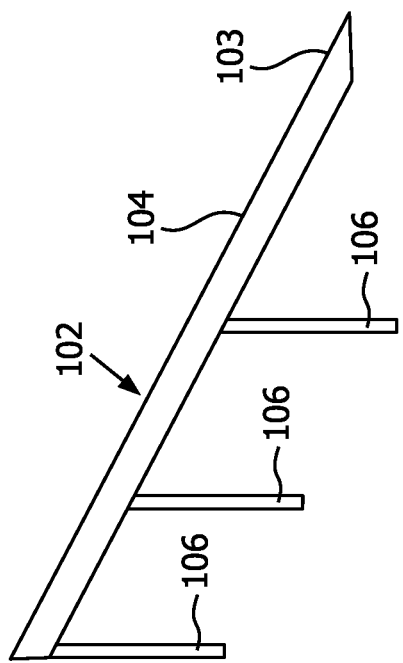
FIG. 10 is a top view showing the device of FIG. 9 with a piezoelectric material being applied to the bottom electrodes in accordance with the present principles.

Referring to FIG. 10, a piezoelectric material 112 (e.g., PVDF or copolymer material) is applied to the cross-strips 106 only. The piezoelectric material 112 may be deposited using masks or the like or may be painted on.

Figure 11:
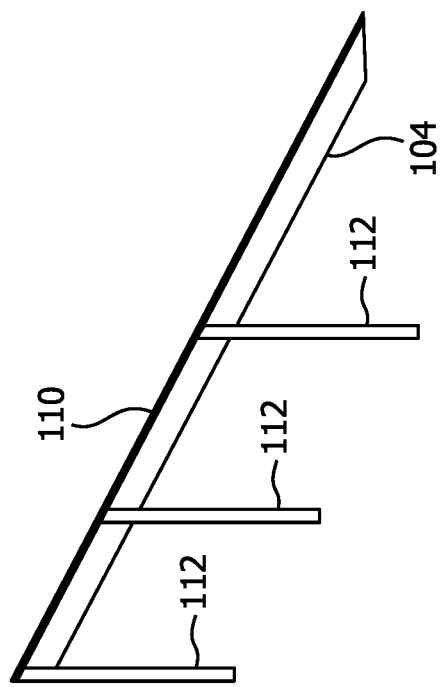
FIG. 11 is a top view showing the device of FIG. 10 with top electrodes (and traces) being applied in accordance with the present principles.

Referring to FIG. 11, a top electrode or electrodes 114 are applied on top of the piezoelectric material 112 and formed along with a trace 116 connecting them and forming sensors 120. In this embodiment, a multi-sensor needle is provided with a shared trace connecting the sensors.

Figure 12:
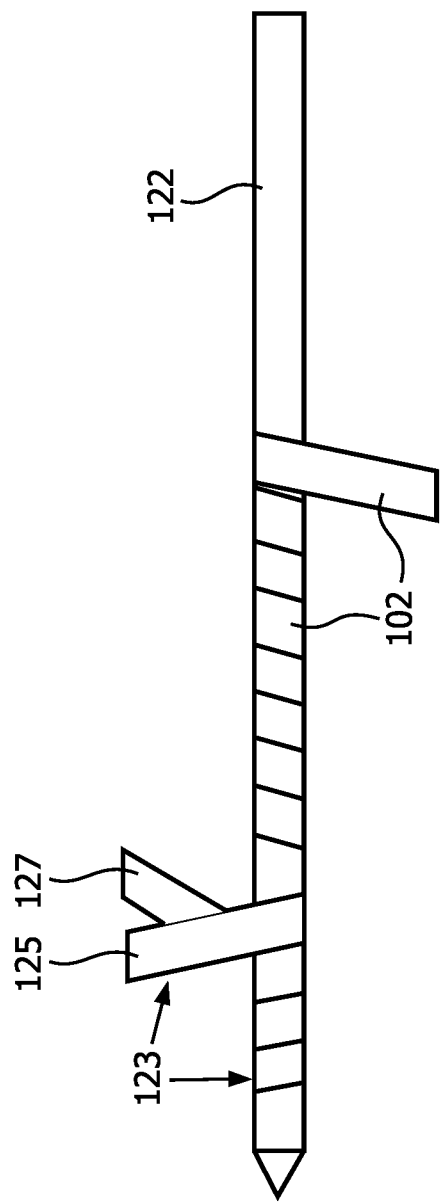
FIG. 12 is a side view showing a spirally wrapped sensor device and a securing feature in accordance with the present principles.

Referring to FIG. 12, the slanted strip 102 can be wound around the needle in a slightly spiraling manner. A first layer that touches a needle 122 can be adhesive in nature. To hold this structure rigidly on the needle 122, a securing feature 123 such as a film may be made in the form of a very narrow strip. This feature 123 includes one or more insulators 125 and a conductive layer 127. The conductive layer 127 may be sandwiched between insulators. The strip 102 (and/or the feature 123) is wound around the needle 122 in a tightly packed dense spiral that fully covers the needle 122. The feature 123 includes an outer biocompatible insulation layer 125, and an outer shield (conductive layer 127). The inner insulator (not shown) of this feature 123 can be adhesive in nature.

Alternate embodiments may include, for example, a structure where the sensors are directly in contact with a needle where the needle functions as one electrode (as in FIG. 7). In other embodiments, a partially elastic tube with interconnects with piezoelectric sensors deposited on the tube may be employed.

In one embodiment, the structure 40 of FIG. 5 could be attached to a needle in a spiral as in FIG. 12. A very narrow adhesive strip could be spiraled around the structure 40 in FIG. 6, this strip could form the outer biocompatible insulator (so the layer 30 in FIG. 5 would no longer be needed). Instead of the narrow adhesive strip, a thin wire may be used to spiral around the structure 40 in FIG. 6. The wire may have an adhesive coating or a non-adhesive wire may be employed followed by dipcoating in a biocompatible glue/encapsulant.

In one embodiment, a tube, such as a heatshrink tube or similar material, such as a material that shrinks when exposed to a chemical or UV light may be employed to encapsulate a strip (spiraled or wrapped) in accordance with the present principles.

In other embodiments, the sensors may include PVDF or copolymer, or the sensors may include, for example, PZT or another piezoelectric material, or an altogether different sensor, such as, a capacitive micromachined ultrasound transducer (CMUT).

In one embodiment, an adhesive layer could be applied to the needle, and the strips or structures described may be pressed around or spiraled around the needle to adhere them.

To keep the product cost down, the materials used should be low cost, and the manufacturing process should be highly automated with large volume to avoid labor and equipment cost. Given these goals, piezoelectrical polymers such as PVDF and P(VDF-TrFE) are candidate materials for sensor production. The ability of an applied voltage to produce motion in a PVDF sample is used to produce ultrasonic waves which can be detected using a PVDF based hydrophone. There are a wide variety of considerations in deciding whether to use a ceramic based piezoelectric or PVDF in a given medical application. At lower frequencies thicker PVDF membranes should be employed for resonance considerations. A PVDF sensor can be modeled as a voltage source in series with a capacitance and for thicker sensors with small surface area. This results in a small capacitance. Hence, in general, it appears that PVDF has advantages for medical ultrasonic work carried out in the frequency range 25-100 MHz. PVDF is also limited in ability to transmit higher intensities of ultrasound compared to PZT.

PVDF has favorable behavior even at the lower frequencies, for example, for PVDF hydrophones for detecting ultrasonic waves. Compared to PZT, which may also be employed in some embodiments, PVDF has a much higher bandwidth and will thus not distort the transient behavior of the wave as much. The low output capacitance problem can in this case be handled by integrating a high input impedance field effect transistor (FET) based preamplifier in very close proximity to the sensor. The d33 constant, strain in thickness direction developed for an applied voltage, is about an order of magnitude higher for piezo-ceramics than for piezo-polymers. One disadvantage of piezo-ceramic is its high acoustic impedance, about 30 MRayls (1 MRayl=106 kg/m$^2$ s) in contrast to about 1.5 MRayls for body tissue. This impedance mismatch can be compensated by quarter wavelength matching layers, but these can degrade the ultrasonic pulse due to adhesive layers and construction methods. The acoustic impedance of piezo film is about 4 MRayls, a much better match. Additionally, ceramics are fragile, and cannot be shaped to desired geometries. PVDF is a conformable and flexible low cost material with acoustic impedance close to tissue that unlike PZT will not need matching layers.

PVDF piezoelectric films are produced in a clean room environment, and start with a melt extrusion of PVDF resin pellets into sheet form. Next, there is a stretching step that reduces the sheet thickness by about a factor of 5. This stretching, well below the melting point of the polymer, causes chain packing of the molecules into parallel crystal planes, called the "beta phase". To obtain high levels of piezoelectric activity, the beta phase polymer is then exposed to very high electric fields to align the crystallites relative to a poling field. In the stretching step, the film can be stretched along only one dimension (uni-axial film) or in both dimensions (bi-axial film). Bi-axial films will have their piezoelectric sensitivity primarily only in the thickness direction, while the uni-axial film will be sensitive to strain in both the thickness direction and the non-stretched planar direction.

New copolymers of PVDF have been developed that allow for use at higher temperatures (e.g., as high as 135 degrees Celsius for some copolymers, versus 100 degrees Celsius for conventional PVDF). Although these temperatures are not encountered in clinical use, a higher temperature tolerance can be an advantage in simplifying the manufacturing and sterilization process. Copolymers of PVDF are polarizable without stretching and very thin films down to 200 Angstroms can be produced using spincast coating techniques, such thin layers are not feasible with standard PVDF. In addition the copolymer has a slightly higher thickness mode piezoelectric constant, leading to about 10% higher sensitivity compared to PVDF.

The present principles have been described in terms of a needle, and more particularly to a biopsy needle. However, the present principles may be applied to nay instrument where a piezoelectric sensor (receiver), transmitter or transducer is needed. Such devices may include catheters, guidewires, endoscopes, implantable devices, etc. The present principles can provide a relatively low cost device with a built-in for sensor conformally applied to an exterior surface. To keep the product cost down, the materials used need to be low cost, and the manufacturing process should be highly automated with large volume to avoid labor and equipment cost. The devices in accordance with the present principles provide a low form factor that is conformally formed and placed on a medical device or instrument. In particularly useful embodiments, the present principles are employed for ultrasound guided needle interventions, e.g., RF ablation, liver biopsy, nerve blocks, vascular access, abscess drainage, etc.

Figure 13:
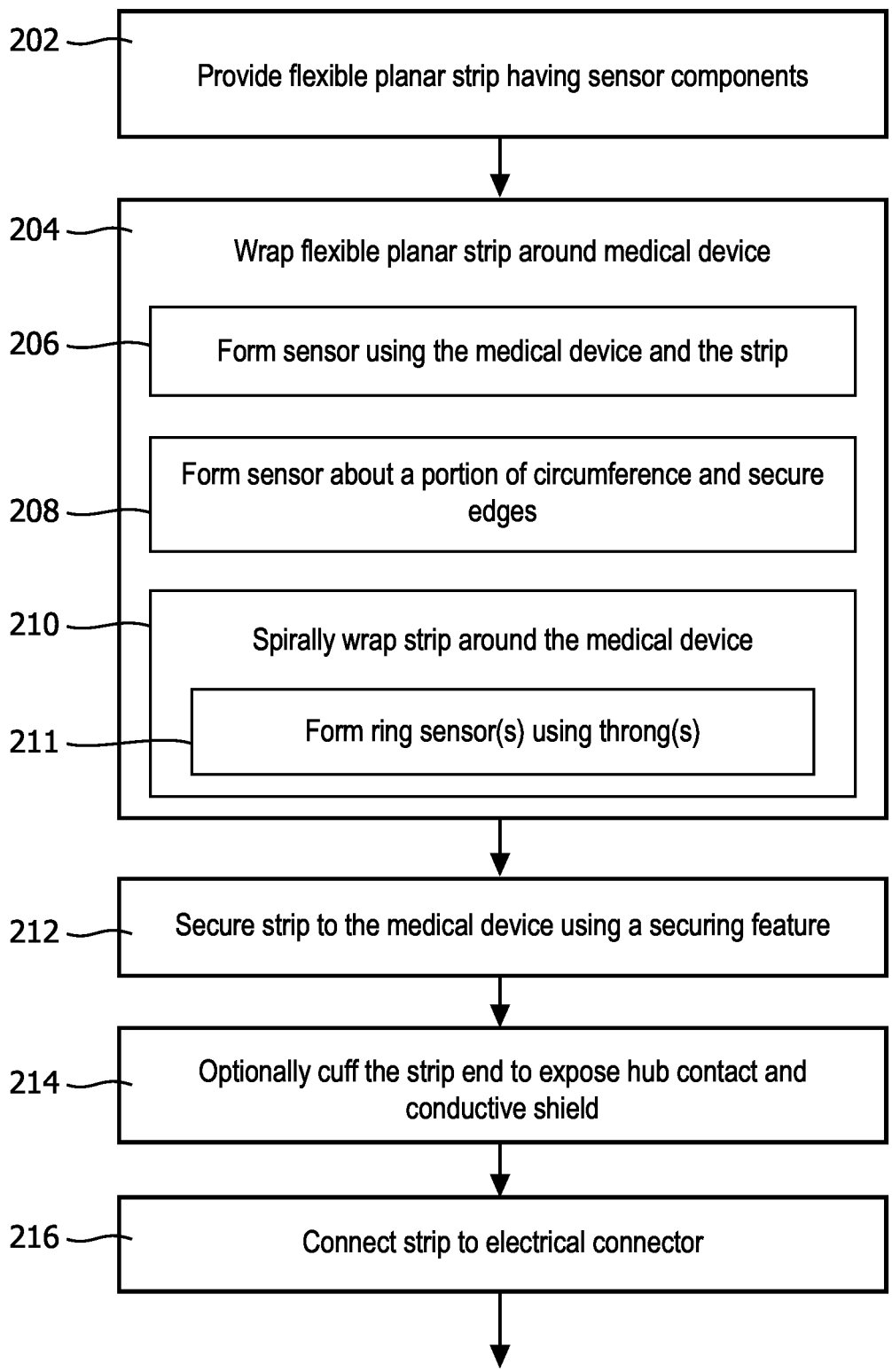
FIG. 13 is a flow diagram showing a method for applying a sensor device in accordance with illustrative embodiments.

Referring to FIG. 13, methods for applying a sensor to a medical device are illustrative shown. In block 202, a flexible planar strip having a plurality of layers including dielectric materials and sensor components is provided in accordance with the present embodiments. The sensor components may be completely on the strip, or partially on the strip and partially on the medical device In block 204, the flexible planar strip is wrapped about a medical device to at least partially encapsulate the medical device. In block 206, the flexible planar strip may be wrapped around a medical device, e.g., a needle, having a piezoelectric polymer coating such that a sensor electrode on the strip contacts the piezoelectric polymer to form the at least one sensor. In block 208, the flexible planar strip is wrapped about at least a portion of a circumference of the device wherein the securing feature is configured to secure edges of the strip over the medical device. In block 210, the flexible planar strip is spirally wrapped about the medical device. In block 211, the flexible planar strip may include at least one cross-strip that forms an angle with the strip such that when the strip is spiraled about the medical device, the cross-strip forms a ring sensor around the medical device.

In block 212, the strip is secured to the medical device using a securing feature over the strip such that at least one sensor device is provided on the medical device by application of the strip on the medical device. In one embodiment, the securing feature is configured to wrap around the strip and includes a conductor to form a shield and at least one dielectric layer (e.g., for the spirally wrapped embodiment). The conductor may include a wire with or without adhesive or dielectric thereon.

In block 214, the strip may include a conductive shield and a hub electrode on a proximal end portion, the conductive shield and the hub electrode may be cuffed to permit external electrical connections to the conductive shield and the hub electrode.

In block 216, an external connector is applied to electrically connect the sensor to electronics. The sensor or sensors can now be employed to make measurements. In particularly useful embodiments, the sensors measure ultrasonic energy for guided needle applications. Other applications and devices are also contemplated.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for needle with thin film piezoelectric sensors (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A sensor device for applying a sensor to a medical device, the sensor device comprising:
 a flexible planar strip configured to at least partially encapsulate the medical device, the flexible planar strip comprising:
  a first dielectric layer;
  a second dielectric layer;
  a patterned conductive layer disposed on the second dielectric layer, the patterned conductive layer including a sensor electrode disposed at a distal end portion of the patterned conductive layer, a hub electrode disposed at the proximal end of the patterned conductive layer, and a trace connecting the sensor electrode and the hub electrode;
  an ultrasound sensor disposed on the sensor electrode, a first surface of the ultrasound sensor configured to make electrical contact with the sensor electrode and a second surface of the ultrasound sensor exposed for making electrical contact with the medical device; and
  a third dielectric layer formed on the patterned conductive layer, wherein a distal end portion of the third dielectric layer is recessed to expose the sensor electrode and a proximal and portion of the third dielectric layer is recessed to expose the hub electrode.

2. The device as recited in claim 1, wherein:
 the ultrasound sensor comprises a piezoelectric polymer;
 the medical device comprises a needle having a piezoelectric polymer, and
 the flexible planar strip is configured to wrap around the needle such that the sensor electrode contacts the piezoelectric polymer of the needle and the needle forms a bottom electrode.

3. The device as recited in claim 1, further comprising a conductive shield layer disposed on the first dielectric layer.

4. The device as recited in claim 3, wherein the second dielectric layer is recessed at a proximal end portion of the second dielectric layer to expose a proximal end portion of the conductive shield layer.

5. The device as recited in claim 1, wherein the first dielectric layer has a width equal to a circumference of the medical device and at least one other layer of the flexible planar strip has a width less than the circumference of the medical device.

6. The device as recited in claim 1, wherein the flexible planar strip is configured to spirally wrap around the medical device to at least partially encapsulate the medical device.

7. The device as recited in claim 1, wherein the first dielectric layer has at least one angled end portion and at least one cross-strip extending transversely from a longitudinal dimension of the flexible planar strip.

8. The device as recited in claim 7, wherein the at least cross-strip forms an angle relative to an axis of the flexible planar strip such that, when the flexible planar strip is spirally wrapped about the medical device, the cross-strip forms a ring around the medical device on the first dielectric layer.

9. The device as recited in claim 1, further comprising:
a bottom electrode and a bottom electrode trace connecting to the bottom electrode, the bottom electrode and the bottom electrode trace formed on the first dielectric layer;
a piezoelectric layer formed on the bottom electrode; and
a top electrode and a top electrode trace connecting to the top electrode, the top electrode and the top electrode trace formed on the piezoelectric layer.

10. The device as recited in claim 9, wherein the flexible planar strip is configured to wrap around the medical device such that the first dielectric layer is in contact with the medical device.

11. The device as recited in claim 1, further comprising: an elongated securing feature configured to wrap around the flexible planar strip, the securing feature including a conductor configured to form a shield and at least one dielectric layer.

12. The device as recited in claim 11, wherein the elongated securing feature includes a wire.

13. A system comprising:
a medical device; and
a flexible planar strip wrapped around the medical device and at least partially encapsulating the medical device, the flexible planar strip comprising:
a first dielectric layer;
a second dielectric layer;
a patterned conductive layer disposed on the second dielectric layer, the patterned conductive layer including a sensor electrode disposed at a distal end portion of the patterned conductive layer, a hub electrode disposed at the proximal end of the patterned conductive layer, and a trace connecting sensor electrode and the hub electrode;
an ultrasound sensor disposed on the sensor electrode a first surface of the ultrasound sensor configured to make electrical contact with the sensor electrode and a second surface of the ultrasound sensor exposed for making electrical contact with the medical device; and
a third dielectric layer formed on the patterned conductive layer, wherein a distal end portion of the third dielectric layer is recessed to expose the sensor electrode and a proximal end portion of the third dielectric layer is recessed to expose the hub electrode.

14. The system as recited in claim 13, wherein the medical device comprises a needle.

15. The system as recited in claim 13, wherein:
the ultrasound sensor comprises a piezoelectric polymer;
the medical device has a piezoelectric polymer, and
the flexible planar strip is wrapped around the medical device such that the sensor electrode contacts the piezoelectric polymer of the medical device and the medical device forms a bottom electrode.

16. The system as recited in claim 13, further comprising a conductive shield layer disposed on the first dielectric layer.

17. The system as recited in claim 16, wherein the second dielectric layer is recessed at a proximal end portion of the second dielectric layer to expose a proximal end portion of the conductive shield layer.

18. The system as recited in claim 13, wherein the wrapped flexible planar strip is spirally wrapped around the medical device.

19. The system as recited in claim 13, wherein:
the first dielectric layer has at least one angled end portion and at least one cross-strip extending transversely from a longitudinal dimension of the flexible planar strip, and
the at least cross-strip forms an angle relative to an axis of the flexible planar strip such that the flexible planar strip wrapped spirally about the medical device forms the cross-strip in a ring around the medical device on the first dielectric layer.

20. The system as recited in claim 13, further comprising a bottom electrode and a bottom electrode trace connecting to the bottom electrode, the bottom electrode and the bottom electrode trace formed on the first dielectric layer;
a piezoelectric layer formed on the bottom electrode; and
a top electrode and a top electrode trace connecting to the top electrode, the top electrode and the top electrode trace formed on the piezoelectric layer.

* * * * *